United States Patent
Nauman

(10) Patent No.: US 11,143,642 B2
(45) Date of Patent: Oct. 12, 2021

(54) GRAPHENE-BASED INDICATOR

(71) Applicant: Brady Worldwide, Inc., Milwaukee, WI (US)

(72) Inventor: J. Michael Nauman, Little Rock, AR (US)

(73) Assignee: Brady Worldwide, Inc., Milwaukee, WI (US)

( * ) Notice: Subject to any disclaimer, the term of this patent is extended or adjusted under 35 U.S.C. 154(b) by 336 days.

(21) Appl. No.: 16/262,511

(22) Filed: Jan. 30, 2019

(65) Prior Publication Data
US 2020/0240969 A1    Jul. 30, 2020

(51) Int. Cl.
| G01N 33/00 | (2006.01) |
| G01N 27/27 | (2006.01) |
| G01N 27/12 | (2006.01) |

(52) U.S. Cl.
CPC ....... *G01N 33/0063* (2013.01); *G01N 27/121* (2013.01); *G01N 27/125* (2013.01); *G01N 27/27* (2013.01); *G01N 33/0052* (2013.01)

(58) Field of Classification Search
None
See application file for complete search history.

(56) References Cited

U.S. PATENT DOCUMENTS

| 10,002,317 | B1 | 6/2018 | Nauman |
| 2011/0297541 | A1 | 12/2011 | Jayatissa |
| 2012/0270205 | A1 | 10/2012 | Patel et al. |
| 2013/0018599 | A1 | 1/2013 | Peng |
| 2014/0073860 | A1 | 3/2014 | Urtti |
| 2014/0121557 | A1 | 5/2014 | Gannon et al. |
| 2015/0268208 | A1 | 9/2015 | Rhodes et al. |
| 2016/0238547 | A1 | 8/2016 | Park et al. |
| 2017/0176370 | A1 | 6/2017 | Velasquez-Garcia et al. |
| 2017/0234820 | A1 | 8/2017 | Lettow |
| 2018/0058940 | A1 | 3/2018 | Lawler, Jr. |
| 2018/0224443 | A1 | 8/2018 | Swager et al. |

FOREIGN PATENT DOCUMENTS

WO    2018182481 A1    10/2018

OTHER PUBLICATIONS

PCT International Search Report and Written Opinion, PCT/US2020/013908, dated Apr. 1, 2020, 11 pages.

*Primary Examiner* — Lisa M Caputo
*Assistant Examiner* — Nigel H Plumb
(74) *Attorney, Agent, or Firm* — Quarles & Brady LLP

(57) ABSTRACT

A sensor product for detecting an analyte or condition. The sensor product having a body and a circuit integrated with the body. The circuit including an electric power source, a sensing element comprising graphene or a graphene derivative in which the sensing element is configured to undergo a change in an electrical property in the presence of an analyte or condition, and an indicator configured to display information indicating the presence of the analyte or condition when the change in an electrical property of the sensing element occurs. For instance, the indicator may display "DANGER EVACUATE" in the presence of chlorine gas, elevated temperatures, or other analytes or conditions.

26 Claims, 4 Drawing Sheets

GRAPHENE-BASED INDICATOR

CROSS-REFERENCE TO RELATED APPLICATION

Not applicable.

STATEMENT OF FEDERALLY SPONSORED RESEARCH OR DEVELOPMENT

Not applicable.

BACKGROUND

This disclosure generally relates to environmental and product sensors, and more particularly to compact sensors that provide an indication to a user.

Providing information by monitoring environments and products for the presence of various analytes or conditions can be useful to producers and distributors when transferring perishable products. In addition to such quality control applications, monitoring the presence of harmful analytes can also be extremely valuable for maintaining safe working environments and preventing pollution.

Previous sensor systems have often used complex constructions when monitoring environments and products. For example, previous assemblies have used integrated wireless communicators, bulky battery sources, biological materials, and intricate circuitries.

These expensive components are known to add additional functionality and/or reliability, but have been cost prohibitive, preventing sensors from being implemented in many processes.

SUMMARY

In view of the above, there is a need for novel sensor constructions that allow for simplified, cost-effective monitoring of analytes and conditions.

The present disclosure addresses the aforementioned issues by providing economical sensor constructions that have a sensing element and indicator that are directly integrated into the sensor product. The sensing element can rely on a graphene-based material configured to undergo a change in an electrical property in the presence of an analyte or condition. By combining the unique sensing properties of graphene and an indicator that is directly integrated with the sensor product, a cost-effective, compact construction is achieved.

In one aspect, a sensor product for detecting an analyte is provided. The sensor product comprising a body and a circuit integrated with the body. The circuit includes an electric power source, a sensing element comprising graphene or a graphene derivative in which the sensing element is configured to undergo a change in an electrical property in the presence of an analyte or condition, and an indicator configured to display information indicating the presence of the analyte or condition when the change in an electrical property of the sensing element occurs.

In another aspect, a method of sensing an analyte or condition is provided. An electrical property is monitored in a sensing element comprising graphene or a graphene derivative in which the sensing element is configured to undergo a change in an electrical property in the presence of an analyte or condition. Information is displayed indicating the presence of the analyte or condition when the change in an electrical property of the sensing element occurs. The information is displayed by an indicator on a sensor body to which the sensing element is integrated.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

DETAILED DESCRIPTION

In the following detailed description, reference is made to the accompanying drawings that form a part hereof. The example embodiment described in the detailed description, drawings, and claims is not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

Figure 1A:
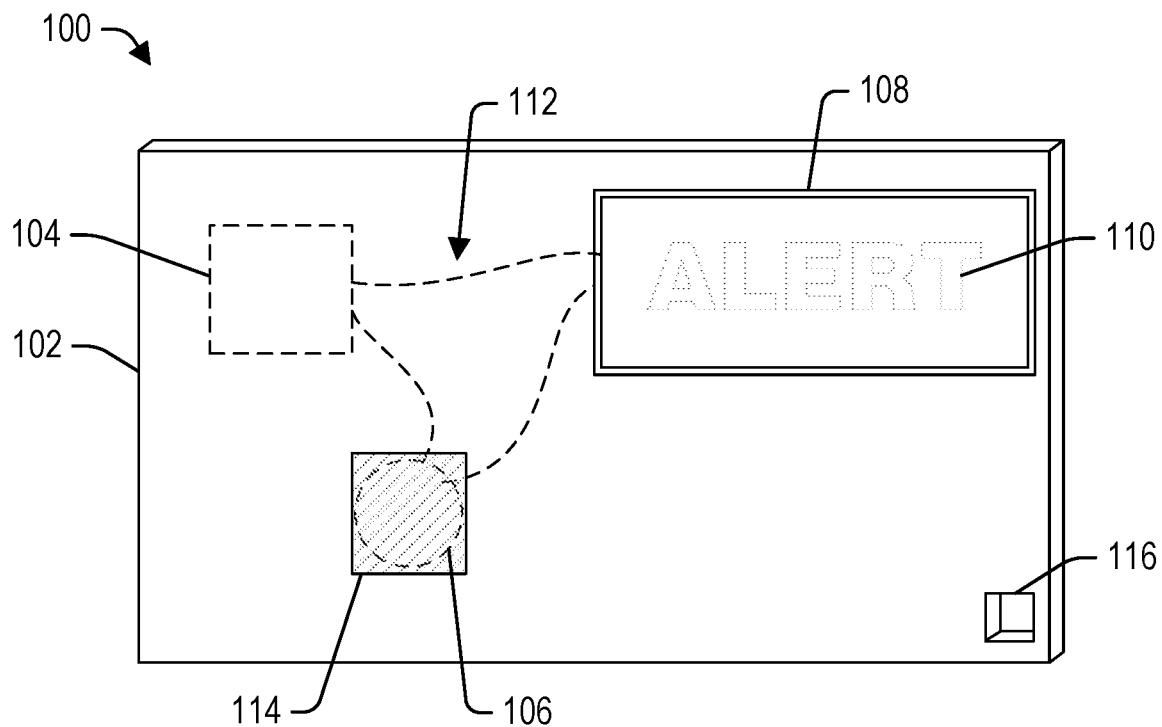
FIG. 1A is a schematic representation of a sensor product in accordance with one aspect of the present disclosure. Internal components are represented with dotted lines.

Referring first to FIG. 1A, a schematic representation of a sensor product 100 is illustrated. The sensor product 100 has a body 102 and a circuit 112 integrated with the body 102. The circuit 112 may be positioned within, or on the exterior of, the body 102 in whole or in part. The circuit 112 includes an electric power source 104, a sensing element 106, and an indicator 108 in electrical communication with one another. The indicator 108 includes a display element 110. In this depiction, the electric power source 104 and sensing element 106 are both positioned within the body 102. However, it is contemplated that the sensing element 106 might, for example be disposed on an exterior of the body 102. As depicted, a filter 114 is positioned between the sensing element 106 and the environment surrounding the sensor product 100. The sensor product 100 also includes an attachment element 116 in the form of an aperture.

As some examples, the body 102 may be a tag, sticker, or label, a card, or may be a container. The body may be formed of a flexible polymer or comparable material. The body may be disposable or reusable. Although an aperture is depicted for the attachment element 116, various alternative components such as hooks, fasteners, and adhesives may be used to attach the sensor product to an external object. The attachment element may allow the sensor product to be placed in close proximity with an object or person of interest. For example, the attachment element may attach the sensor product to a worker, location in a manufacturing center, a shipping container, or a product. The unique component and material choices of the sensor product allow the body to have a compact size. For example, the body may be sized to fit within a 9 cm by 9 cm by 1 cm container, a 9 cm by 9 cm by 0.5 cm container, a 4 cm by 4 cm by 1 cm container, or a 4 cm by 4 cm by 0.5 cm container. The reduced size in comparison to previous systems will allow for new applications and placements of the sensor product.

The electric power source 104 may be configured to apply a voltage to the circuit 112. The electric power source may be a battery. More specifically, the electric power source may be a thin film or printed battery. In order to determine a change in an electrical property of the sensing element, an electric current may be applied. The electric power source may configured to continuously apply such a current. Alternatively, the electric power source may repeatedly provide an electrical pulse of the current after a time interval. The time interval may be selected from the group consisting of between 0.1 second and 1 second, between 1 second and 10 seconds, between 10 seconds and 1 minute, between 1 minute and 0.1 hour, between 0.1 hour and 1 hour, between 1 hour and 10 hours, between 10 hours and 24 hours, and between 24 hours and 168 hours.

The sensing element 106 may comprise graphene or a graphene derivative. For example, the sensing element may comprise pure graphene, graphene oxide, reduced graphene oxide. The sensing element may be in the form of a rod, thin film, block, or another suitable shape. The sensing element may be a functionalized form of graphene or a graphene derivative. The sensing element may be configured to undergo a change in an electrical property in the presence of an analyte or condition. The change may be brought on as a result of a reaction of the sensing element as a result of the analyte or the condition of the environment surrounding the sensor product. The electrical property may be the resistance, impedance, or capacitance. In some forms, the change in an electrical property may specifically be an increase or decrease of the resistance of the sensing element. The sensing element may be functionalized to undergo this change in the presence of a specific analyte.

Figure 1B:
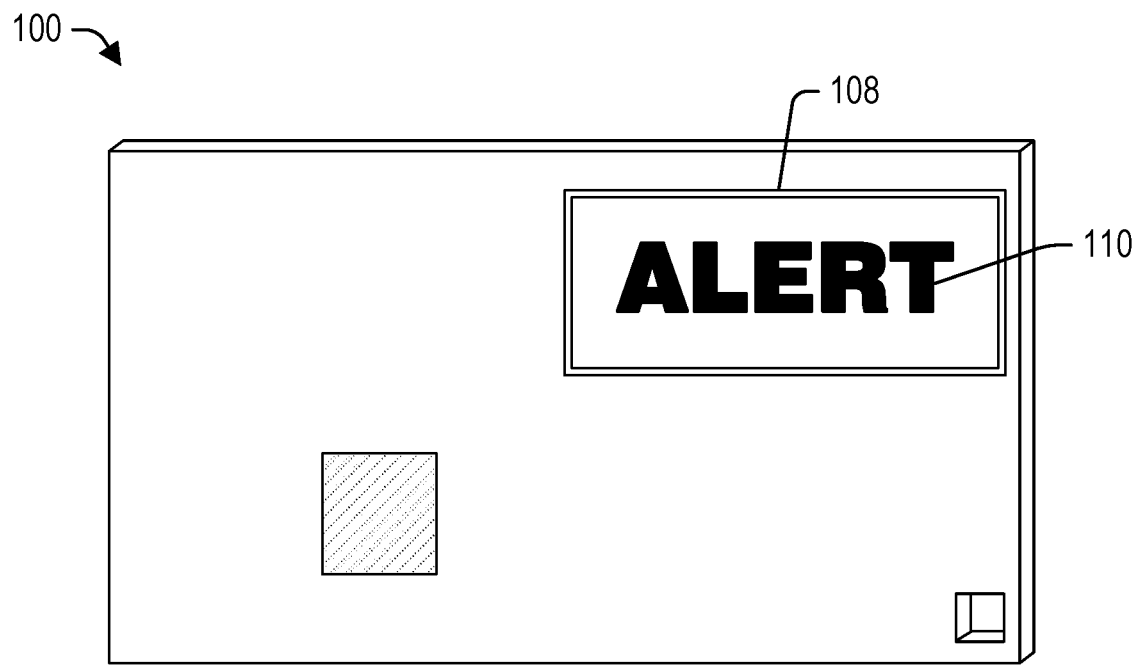
FIG. 1B depicts the sensor product of FIG. 1A in an alert state and displaying information indicating the presence of the analyte or condition. Internal components are not shown in this view.

The indicator 108 may be configured to display information indicating the presence of the analyte or condition when the change in an electrical property of the sensing element occurs. There are a number of means by which the indicator may display this information. The indicator may display a color or tone change of the display element. The color or shade change may be directly representative of the presence of the analyte or condition. The change in color or shade may correspond to the quantity of the analyte that is being detected. Alternatively, the color or tone change may result in the appearance or development of an alert word or symbol. For example, as shown in FIG. 1B, the display element may darken to form a word, such as "ALERT". The word or symbol may be representative of the analyte or condition. For example, words such as "HEAT", "WATER", "CHLORINE", or the like may be used. Alternatively, the display element may provide a generic warning or safety related word, phrase, or symbol that is not indicative of the detected analyte or condition. For instance, the display element may form an alert word such as "DANGER EVACUATE" or "CAUTION" in the presence of chlorine gas or elevated temperatures.

The indicator 108 may utilize a chemical reaction and provide an immediate alert a user. For example, the indicator may be a flare or controlled explosion, which may provide either a bright light or loud sound. Such an indicator may permanently burn, damage, or otherwise alter the sensor product, making the indication permanently visible on the sensor product after the flare or controlled explosion ceases. Alternatively, the indicator may include at least one light, such as a light-emitting diode. Although such alert signals are effective, they require a steady power supply to maintain in an alert state. Consequently, the indicator may alternatively include a device configured to undergo a permanent or semi-permanent change that does not require a continued power supply to maintain. For example, the indicator may comprise an electrochromic or electrophoretic display.

In response to a small electrical voltage, electrochromic materials will change their color. Similarly, electrochromic displays will undergo a change in color or tone when a voltage is applied. An important advantage of using an indicator with an electrochromic or electrophoretic material is the low power usage of these systems. Once a color or shade change has been effected, the new state exists with little or no input of power in what is called a "memory effect". In practice, this may allow the sensor product of the present disclosure to utilize extremely low-cost, compact batteries. The batteries may only be capable of performing a one-time, semi-permanent change of the display element to an alert state, thereby perpetually indicating to a user that the presence of an analyte. This may be particularly useful when monitoring products during shipping over the course of multiple days, an amount of time that would typically require a large capacity power source.

The indicator 108 may be configured to display information indicating the presence of multiple analytes or conditions. For example, the display may turn blue when contacted with liquid water and red when heated to above 35 degrees Celsius. Alternatively, the sensor product may further comprise at least one additional indicator or display element, wherein the additional indicator or display element is configured to display information indicating the presence of a second analyte or condition.

When the sensing element 106 undergoes the specific change in the electrical property, the indicator is configured to display information indicating the presence of the analyte. This interaction may result from a circuit opening or closing as a result of the change in the resistance across the sensing element. The change in the electrical property may open, close, or otherwise alter the properties of circuit to which the sensing element is integrated with. In this manner, the sensor product or the present disclosure may avoid using complex controllers. Factors such as the temperature of the sorbent body, the atmospheric pressure, and the phase, amount, and/or composition of the analyte may affect the change in the electrical property. The sensing elements may be specifically tailored and functionalized to adsorb specific analytes. Consequently, the sensing elements may be used to detect temperature changes, liquid detection, the presence of specific analytes, as well as other stimuli. The detected analyte may be in the form of a vapor. The analyte may specifically be a hazardous vapor, such as a chlorine. In some aspects, the analyte may be a harmful volatile organic compound, such as benzene.

If a filter 114 is present, the filter 114 may be positioned between the sensing element 106 and any external environment. The filter may configured to prevent certain compounds from contacting the sensing element. For example, the filter may adsorb, absorb, or physically block compounds that may affect a change in electrical property of the sensing component if they are not an analyte of interest.

Figure 2A:
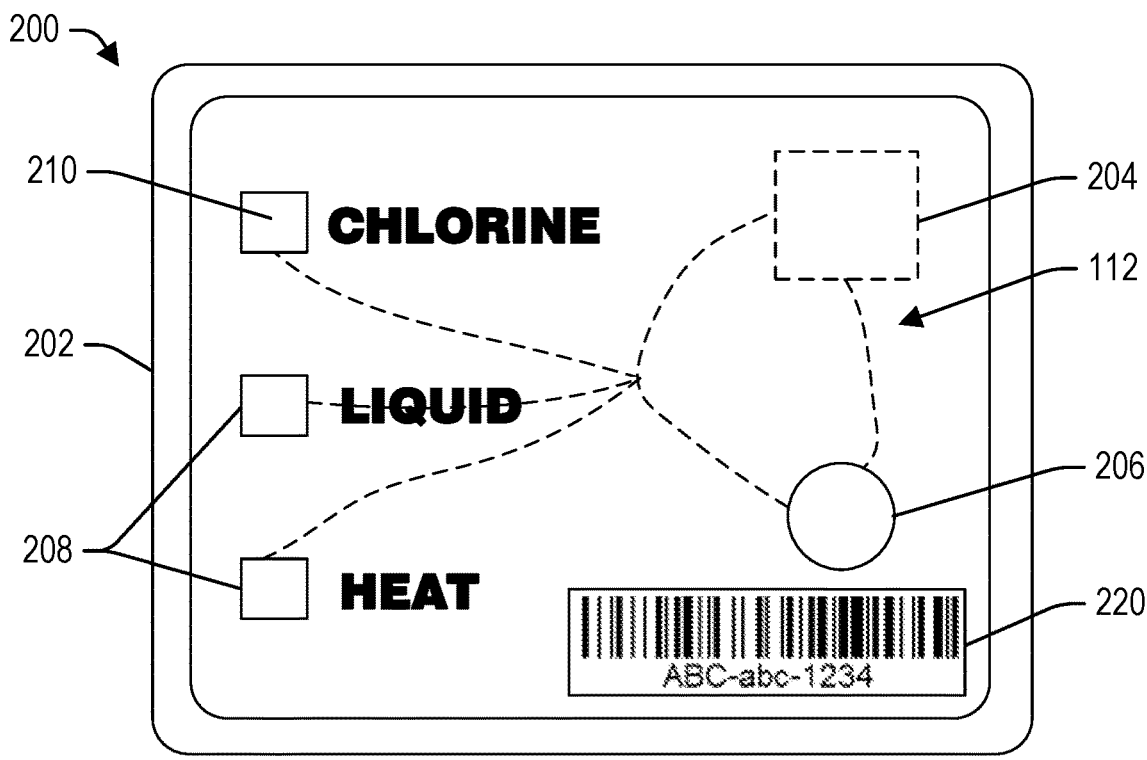
FIG. 2A is a schematic representation of another sensor product. Internal components are represented with dotted lines.

FIG. 2A depicts a schematic representation of another sensor product 200. The sensor product 200 has a body 202, and a circuit 212 integrated with the body 202. The circuit 212 includes an electric power source 204, a sensing element 206, and three indicators 208 in electrical communication with one another. Each of the indicators 208 includes a display element 210. The sensor product 200 also has an identifier 220. The identifier may be a product name, barcode, QR code, or similar identifier. In this depiction, the sensing element 206 is positioned on the exterior of the body 202. This configuration directly exposes the sensing element to the environment surrounding the sensor product 200, which may help improve the accuracy and response time of the product sensor.

Figure 2B:
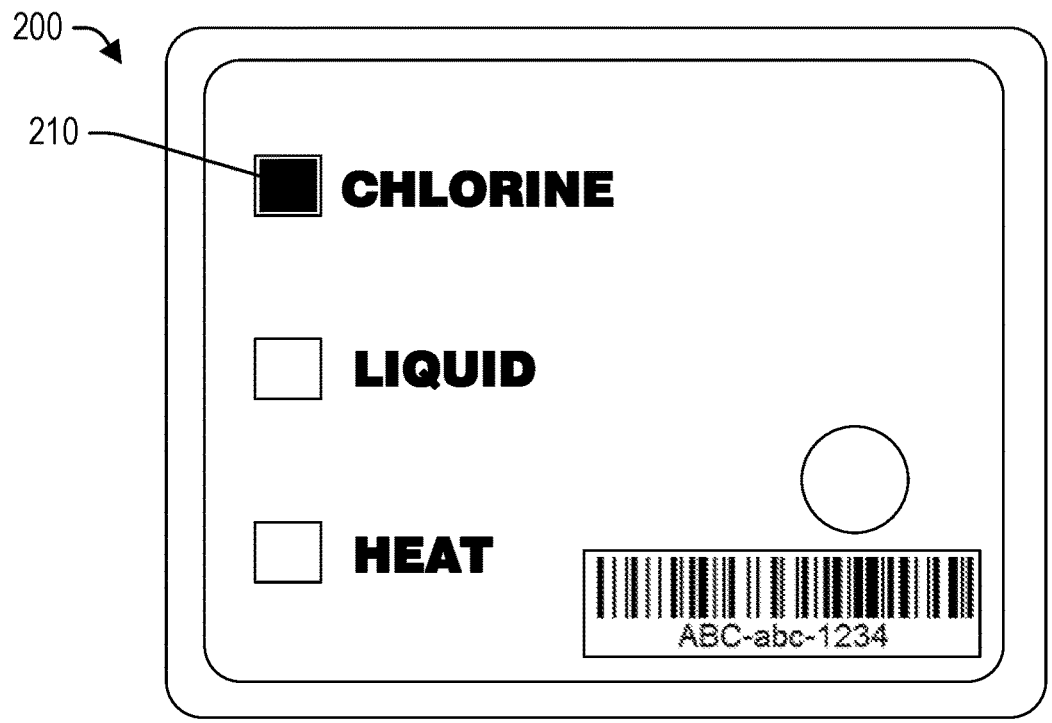
FIG. 2B depicts the sensor product of FIG. 2A in an alert state and displaying information indicating the presence of the analyte or condition. Internal components are not shown in this view.

As shown in FIG. 2B, the sensor product 200 can be used to provide information using three individual indicators and display elements when detecting the presence of a three separate analytes or conditions. In this depiction, each indicator corresponds to a printed term on the sensor product, namely "CHLORINE", "LIQUID", and "HEAT. The circuit 212 may contain components that allow for the sensing and indication of each analyte or condition using only a single sensing element. A change in resistance across the sensing element may vary between various analytes and conditions. Such a change in resistance may only by large enough to trigger a single indicator to change its display element to an alert state. Alternatively, the sensor product may have multiple sensing elements, each functionalized or configured to detect a specific analyte or condition.

Figure 3A:
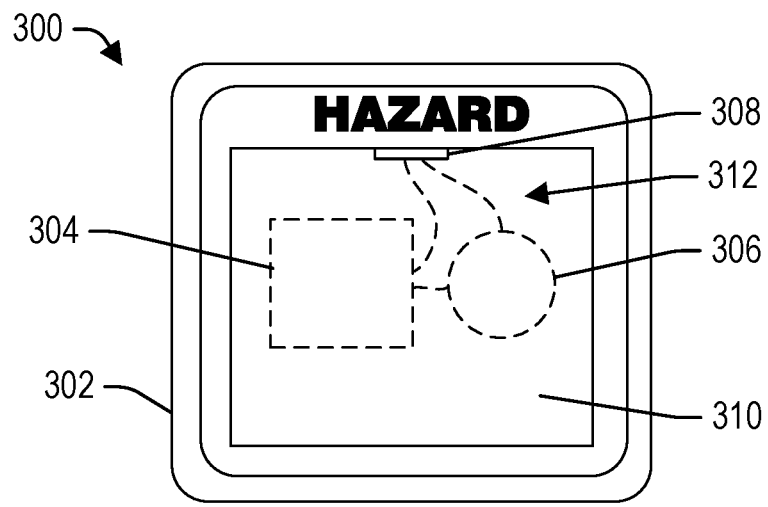
FIG. 3A is a schematic representation of yet another sensor product. Internal components are represented with dotted lines.

FIG. 3A depicts a schematic representation of yet another sensor product 300. The sensor product 300 again has a body 302 and a circuit 312 integrated with the body 302. The circuit 312 includes an electric power source 304, a sensing element 306, and an indicator 308 in electrical communication with one another. The indicators 308 includes a display element 310. In this depiction, the electric power source 304 and sensing element 306 are positioned on the interior of the body 302, behind the display element 310. Although not shown, the exterior face of the body 302, opposite the display element 310, is coated with an adhesive.

Figure 3B:
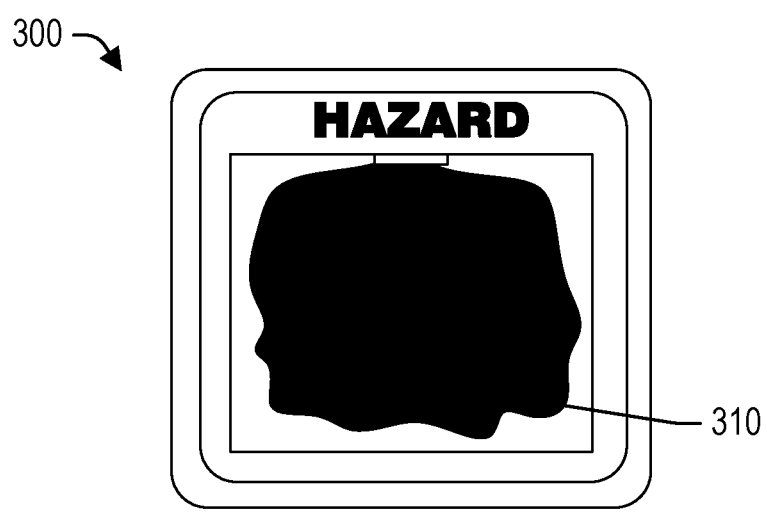
FIG. 3B depicts the sensor product of FIG. 3A in an alert state and displaying information indicating the presence of the analyte or condition. Unlike FIG. 3A, internal components are not shown.

As shown in FIG. 3B, the display element 310 comprises an electrophoretic or electrochromic material. The depicted alert state of the display element may be permanent.

In FIGS. 1-3, the circuit has been represented as dotted lines connecting the respective electric power sources, the sensing elements, and indicators. In general, one of skill in the art will recognize that the circuit, including the sensing element, electric power source, and indicator, may comprise any number of electronic components such as resistors, transistors, capacitors, inductors and diodes, processors, conductive wires or traces through which electric current can flow, and additional electronic components in order to achieve the described functionality.

Figure 4:
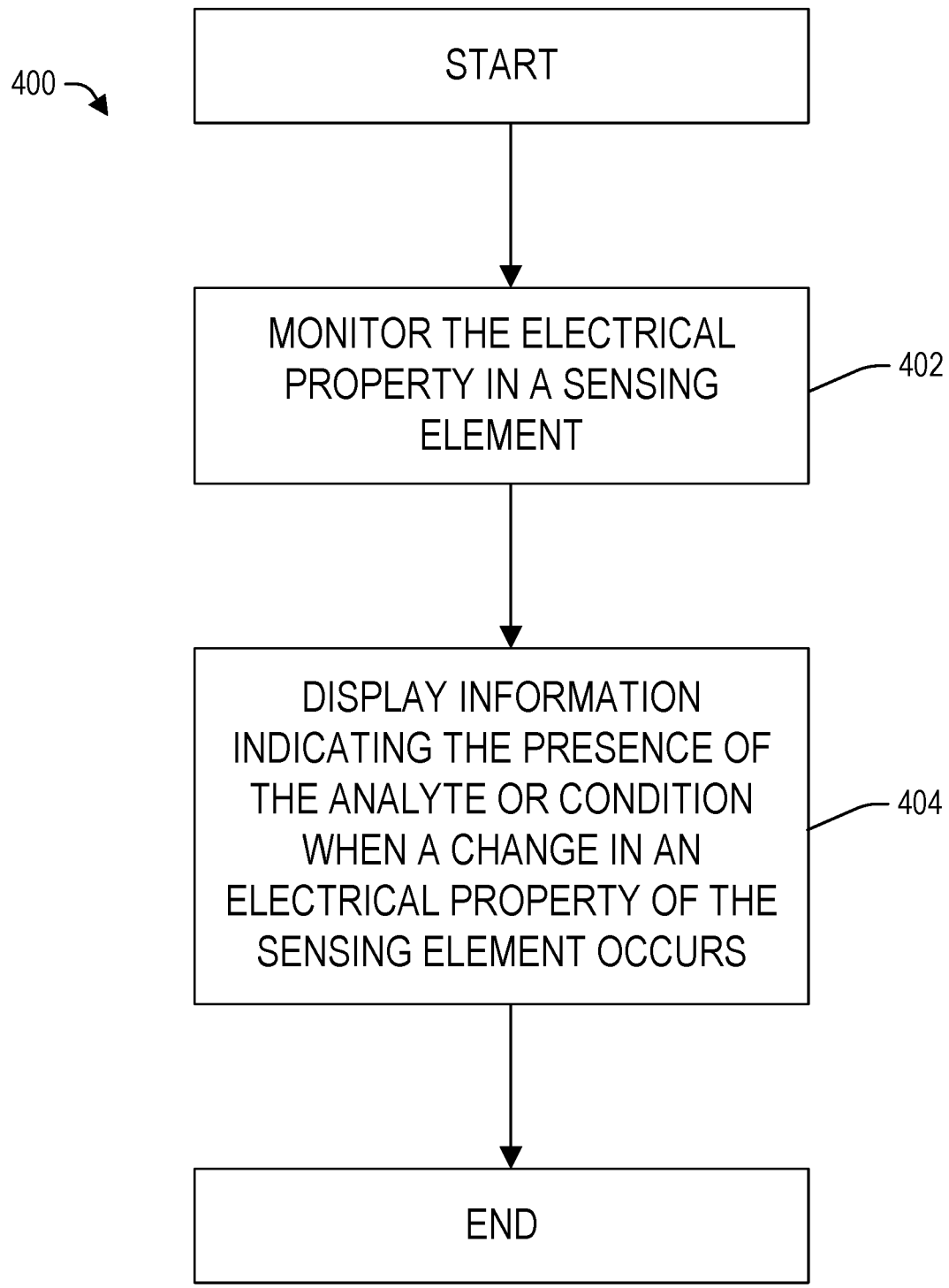
FIG. 4 is a flow chart providing a method of using a sensor of the types described above.

As shown in FIG. 4, a method 400 of sensing an analyte or condition is provided. The method may comprise the steps of monitoring the electrical property in a sensing element comprising graphene or a graphene derivative, the sensing element configured to undergo a change in an electrical property in the presence of an analyte or condition 402 and displaying information indicating the presence of the analyte or condition when the change in an electrical property of the sensing element occurs, the information being displayed by an indicator on a sensor body to which the sensing element is integrated 404. The method may utilize the sensor product configurations and materials described herein. The method may further comprise attaching the sensor body to a region of interest In yet another aspect, a method of making the sensor product described herein is provided, the method comprising assembling the sensor product.

It will be appreciated that in the sensor products described herein, once the analyte or condition of interest is detected, this may trigger another reaction or condition which results in the indication of the condition being satisfied. In such instances, the chemical or electrical change detected may be relatively small and the detection of the condition can be used to trigger response involving a greater expenditure of energy to provide the indication. Put differently, the size of the energy associated the detection condition may be much smaller than the energy expended during the triggering event that results in the provided indication.

As noted above, it should be appreciated that various other modifications and variations to the preferred embodiments can be made within the spirit and scope of the invention. Therefore, the invention should not be limited to the described embodiments. To ascertain the full scope of the invention, the following claims should be referenced.

What is claimed is:

1. A sensor product for detecting an analyte or condition, the sensor product comprising:
   a body; and
   a circuit integrated with the body, the circuit comprising:
      an electric power source;
      a sensing element comprising graphene or a graphene derivative, the sensing element configured to undergo a change in an electrical property in the presence of an analyte or condition; and
      an indicator configured to display information indicating the presence of the analyte or condition when the change in an electrical property of the sensing element occurs wherein the condition is selected from the group consisting of a change in humidity and a change in temperature.

2. The sensor product of claim 1, wherein the indicator displays a color change.

3. The sensor product of claim 2, wherein the indicator comprises an electrochromic material.

4. The sensor product of claim 1, wherein the indicator comprises at least one light-emitting diode.

5. The sensor product of claim 1 further comprising at least one additional indicator, wherein the additional indicator is configured to display information indicating the presence of a second analyte or condition.

6. The sensor product of claim 1, wherein the electric power source is a printed battery.

7. The sensor product of claim 1, wherein the analyte is in the form of a vapor.

8. The sensor product of claim 7, wherein the analyte is a hazardous vapor.

9. The sensor product of claim 8, wherein the analyte is chlorine gas.

10. The sensor product of claim 1, wherein the sensor product is sized to fit within a 9 cm by 9 cm by 1 cm container.

11. The sensor product of claim 1 further comprising a filter configured to prevent certain analytes from contacting the sensing element.

12. The sensor product of claim 1, wherein the indicator displays a generic warning as a word, phrase, or symbol that is not indicative of the analyte or condition.

13. A method of making a sensor product, the method comprising:
assembling the sensor product of claim 1.

14. A method of sensing an analyte or condition, comprising the steps of:
monitoring the electrical property in a sensing element comprising graphene or a graphene derivative, the sensing element configured to undergo a change in an electrical property in the presence of an analyte or condition wherein the condition is selected from the group consisting of a change in humidity and a change in temperature; and
displaying information indicating the presence of the analyte or condition when the change in an electrical property of the sensing element occurs, the information being displayed by an indicator on a sensor body to which the sensing element is integrated.

15. The method of claim 14, wherein displaying information comprises the indicator displaying a color change.

16. The method of claim 15, wherein the indicator comprises an electrochromic material.

17. The method of claim 14, wherein the indicator comprises at least one light-emitting diode.

18. The method of claim 14 further comprising displaying information indicating the presence of a second analyte or condition.

19. The method of claim 14, wherein monitoring the electrical property comprises providing electric power using a printed battery.

20. The method of claim 14, wherein the analyte is in the form of a vapor.

21. The method of claim 20, wherein the analyte is a hazardous vapor.

22. The method of claim 21, wherein the analyte is chlorine gas.

23. The method of claim 14 further comprising attaching the sensor body to a region of interest.

24. The method of claim 14, wherein the indicator displays a generic warning as a word, phrase, or symbol that is not indicative of the analyte or condition.

25. The sensor product of claim 1, further comprising an identifier on the sensor product, the identifier comprising at least one of a product name, barcode, and quick response (QR) code.

26. The method of claim 14, wherein the sensor body has an identifier thereon, the identifier comprising at least one of a product name, barcode, and quick response (QR) code.

* * * * *